United States Patent [19]

McFall et al.

[11] 4,038,701

[45] Aug. 2, 1977

[54] ABOVE THE KNEE PROSTHESIS DONNING DEVICE

[76] Inventors: Jim McFall; Jim Cicero; Tom Phillips, all of 2827 Commerce, Dallas, Tex. 75226

[21] Appl. No.: 716,424

[22] Filed: Aug. 23, 1976

[51] Int. Cl.² .......................... A61F 1/00; A61F 1/02
[52] U.S. Cl. ............................................ 3/1; 3/17 R; 3/17 SS
[58] Field of Search ................ 3/1, 2, 17 R, 17 SS; 128/25 R, 80 R

[56] References Cited

U.S. PATENT DOCUMENTS

| 2,666,927 | 1/1954 | Morheiser | 3/1 |
| 2,966,905 | 1/1961 | Kamenshine | 128/25 R |
| 3,502,071 | 3/1970 | Holly | 128/25 R |
| 3,922,727 | 12/1975 | Bianco | 3/1 |

Primary Examiner—Ronald L. Frinks
Attorney, Agent, or Firm—Hubbard, Thurman, Turner & Tucker

[57] ABSTRACT

A device to aid in donning of an above-the-knee artificial leg is disclosed. The device includes a supporting frame which can be held down by the foot of the artificial leg and a roller supported by the supporting frame which reverses the direction of pull on a donning sock or wrapping bandage.

4 Claims, 3 Drawing Figures

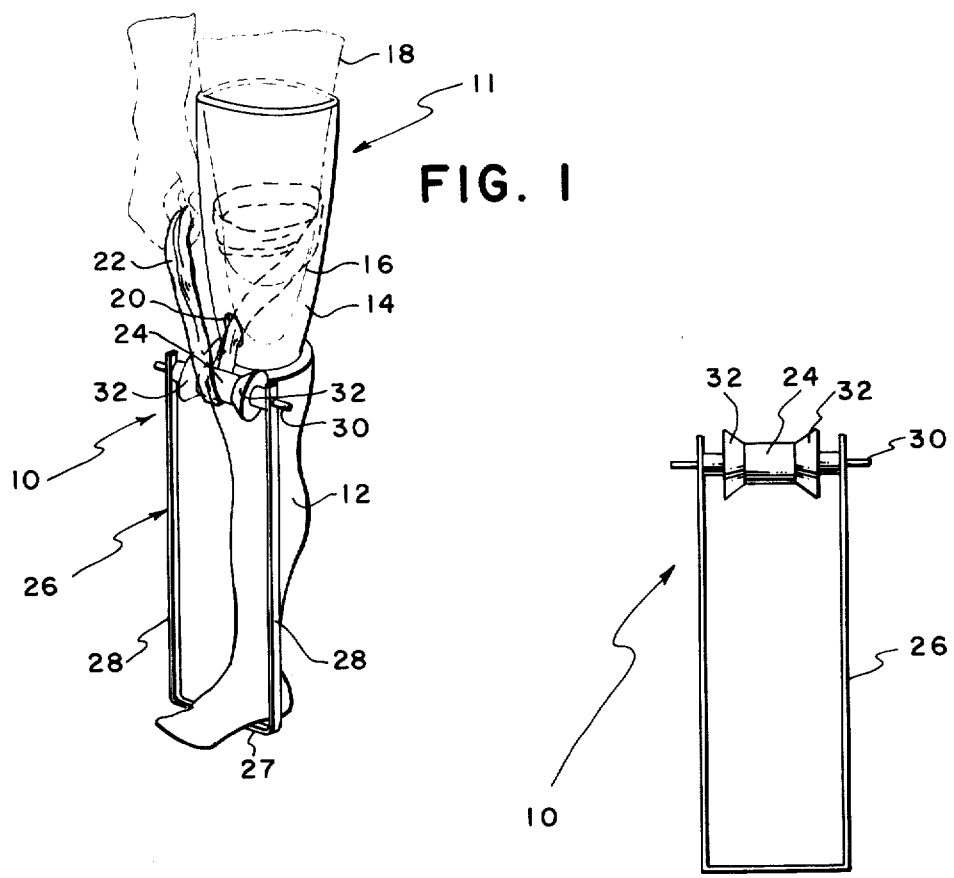
FIG. 1
FIG. 2
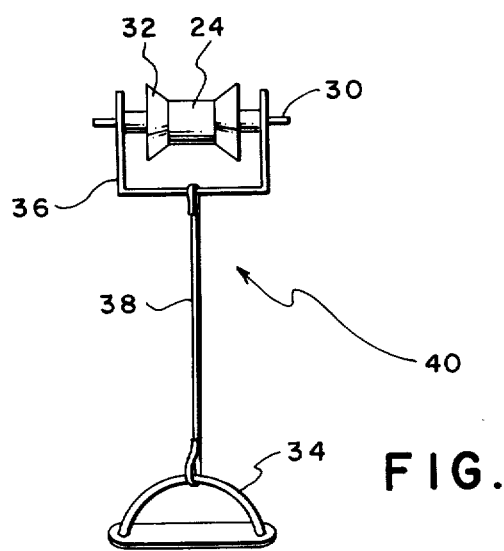
FIG. 3

ABOVE THE KNEE PROSTHESIS DONNING DEVICE

This invention relates to donning devices for aiding persons with artificial legs to insert a leg stump into the artificial leg.

To firmly attach an above-the-knee artificial leg requires a nearly perfect fit between the stump of the leg and the socket in the artificial leg. As a result, it is difficult to get the stump into the socket. To aid in securing an artificial leg, a donning sock consisting of a tubular length of textile material is drawn over the wearer's stump, and the loose end of the donning sock is then inserted through a hole in the knee of the artificial leg. The loose end of the donning sock is pulled through the hole in the knee of the artificial leg, pulling the stump firmly into the socket as the donning sock unwraps.

A major problem that arises with the use of a donning sock is that the sock must be pulled down through the hole in the knee of the artificial leg, meaning that the force pulling the sock must be applied downward from the knee which is in a direction away from the arms and shoulders of the wearer. One attempt to overcome this problem is shown in U.S. Pat. No. 2,666,927 issued to Morheiser. That device included a board on which the person attempting to fit an artificial leg stood with the board under both feet, and a pulley attached to the board. A special donning sock which included a hook and link had to be used along with a cord to be used with the pulley. While the Morheiser device, when properly used, permitted reversal of the direction of pull on the donning sock, it also has a number of disadvantages. The Morheiser device is bulky, it is not easily portable, and requires special donning socks which are not readily available, and they are necessarily more complicated and expensive to make.

Later donning aid devices, such as that shown in U.S. Pat. No. 3,922,727 issued to Bianco, are fully automated. The donning aid device disclosed in the Bianco patent uses a reversible electric motor mounted on a base plate held by both feet, and a hand-held control is provided to operate the motor. While this device is relatively easy to use, it is relatively expensive and too bulky to be readily portable. Further, electromechanical devices are frequently subject to failure and can be dangerous.

A non-automated rachet type donning aid device which attaches to the knee by screwing into the valve adapter located in the knee hole has also been proposed. While this device provides some advantage over hand pulling the donning sock in that the pull stroke is shortened, but it also is relatively expensive and, in addition, wear on the valve threads in the knee hole results. In using such rachet devices, the amputee must still bend over to the knee causing improper placement of the stump within the socket.

It is the object of this invention to provide a relatively inexpensive donning aid device which is conveniently portable and does not require the use of a special donning sock.

The donning device of this invention is designed to aid in pulling the donning sock through the hole in the knee of the artificial leg by reversing the direction of pull on the sock. The device includes a roller which is connected to a foot stirrup which may extend up to support the roller slightly below the knee sock hole, or which may be connected to the roller by a rope or cord adjustable in length. The loose end of the sock is pulled around the roller allowing the amputee to pull the sock from a standing position. The pull on the sock will be upward, thus adding to the ease of donning the artificial leg. The donning aid device of this invention is relatively simple to make and operate, is relatively inexpensive and portable, and doesn't require a special donning sock not readily available on the market. In fact, the donning device of this invention sufficiently eases the donning of an above the knee artificial leg that a wrapping bandage can be used in place of the donning sock, thus reducing costs and problems associated with maintaining and finding a supply of donning socks.

The advantages and features of this invention will be apparent from the following description taken with reference to the accompanying drawings, wherein is shown the preferred embodiments of the invention:

FIG. 1 is a perspective view of a donning device of this invention showing the lower limb of the amputee for explanation purposes;

FIG 2 is a front view of a preferred form of a donning device utilizing this invention; and FIG. 3 is a view in elevation of another embodiment of the donning device of this invention.

In FIG. 1 the donning device embodying this invention is designed generally by the reference numeral 10 and an above the knee artificial leg 11 is illustrated as including a calf member 12 and a thigh member 14. Thigh member 14 of artificial leg 11 includes a socket 16 designed for receiving a leg stump 18 of the person requiring the artificial leg. Thigh member 14 also includes a knee hole 20 which in normal operation accepts a one way valve (not shown) which exhausts air from socket 16 after the leg stump is inserted to permit the leg stump to have a snug fit between the stump and the socket.

As also illustrated in FIG. 1, a length of wrapping bandage 22 or a conventional knee sock or other leg stump wrapping device is placed around the bottom of stump 18. One end of wrapping bandage 22, or the knee sock if used, is pulled through the knee hole 20 for use as an aid in the donning operation as hereinafter explained.

Donning device 10 includes a roller 24 and a U-shaped stirrup 26 which includes a foot bar 27 and upstanding support arms 28. Arms 28 support roller 24 in such a way that the roller can revolve around its central axis and about a support dowel 30 thus allowing the wrapping bandage to be pulled around the roller. The roller, in effect, merely changes the direction of pull on the bandage which is necessary in order to unwrap the bandage from the stump. It is preferred that roller 24 include beveled end portions 32 of the roller 24 to act as a guide to keep the wrapping bandage centered on the spool, but the beveled edges are not necessary for proper operation of device.

To don an artificial leg using the device of this invention, an amputee wraps wrapping bandage 22 around the stump of the leg in either a clockwise or counter-clockwise fashion and slides the stump into the socket 16 so that bandage 22 goes through knee hole 20. He then pulls bandage 22 around roller 24 so that he can then pull the bandage upward with his arms. He then secures the donning device by placing his foot over foot bar. 27. As the amputee continues to pull on bandage 22, it upwraps from stump 18, pulling the stump more and more tightly into socket 16. Once the bandage has completely unwrapped, the stump should be firmly in socket 18 with a relatively tight fit. The amputee can then place the one way valve into knee hole 20 to provide an exhaust for maintaining the proper fit between the stump and the socket. The entire donning operation can be performed while the amputee is in a substantially upright position, thus providing the best possible fit between the stump and the socket.

The supporting member 26 has been shown as substantially rigid, but it could also be flexible. Likewise, a doweled type support has been shown for the roller 24, but other forms of support could be substituted.

Another embodiment of the present invention is designated by the numeral 40 in FIG. 3 wherein elements which are the same as those of the previous embodiment are numbered the same. Foot stirrup 34 is separate from roller support 36 in this embodiment, the two being joined by an adjustable length connector 38. This embodiment of the invention functions in a manner similar to that of the previous embodimemt except that the overall length of the donning aid device could be varied and the device could be taken apart into smaller components for portability.

Roller 24 could be completely replaced by dowel 30 alone or by other means for permitting the direction of pull on the leg stump wrapping device by the person donning the artificial leg to be changed so that the wrapping device can be pulled from a substantially upright position by the person donning the artificial leg.

From the foregoing, it will be seen that this invention is one well adapted to attain all of the ends and objects hereinabove set forth, together with other advantages which are obvious and which are inherent to the apparatus. It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

The invention having been described, what is claimed is:

1. An artificial leg donning aid to be used with a leg stump wrapping device utilized to pull the stump into engagement with the artificial leg comprising, in combination;
    a stirrup adapted to receive only one foot of the person donning such an aritificial leg and further adapted to extend upwardly towards the knee of such an aritificial leg; and
    means adapted to be supported by said stirrup adjacent the knee of the artificial leg for permitting the direction of pull on the leg stump wrapping device by the person donning the artificial leg to be changed so that the wrapping device can be pulled from a substantially upright position by the person donning the artificial leg.

2. An artificial leg donning aid according to claim 1 wherein the means for permitting the direction of pull on the leg stump wrapping device to be changed is a roller for engaging the wrapping device.

3. An artificial leg donning aid according to claim 2 wherein the roller includes beveled end portions.

4. An aritificial leg donning aid according to claim 1 wherein the means for permitting the direction of pull on the leg stump wrapping device to be changed is a dowel for engaging the wrapping device.